(12) United States Patent
Couet et al.

(10) Patent No.: US 6,886,406 B1
(45) Date of Patent: May 3, 2005

(54) DOWNHOLE DEPOSITION MONITORING SYSTEM

(75) Inventors: Benoit Couet, Weston, CT (US); Timothy Gareth John Jones, Cottenham (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 10/088,752

(22) PCT Filed: Oct. 26, 2000

(86) PCT No.: PCT/GB00/04128

§ 371 (c)(1),
(2), (4) Date: Jul. 29, 2002

(87) PCT Pub. No.: WO01/31328

PCT Pub. Date: May 3, 2001

(30) Foreign Application Priority Data

Oct. 27, 1999 (GB) ............................................. 9925373

(51) Int. Cl.[7] ............................ G01H 1/12; G01H 13/00
(52) U.S. Cl. ....................... 73/579; 73/54.24; 73/54.25; 73/1.49; 73/64.53
(58) Field of Search ....................... 73/579, 651, 54.24, 73/54.25, 1.49, 64.53

(56) References Cited

U.S. PATENT DOCUMENTS

| | | | | |
|---|---|---|---|---|
| 3,056,284 A | * | 10/1962 | Marsh et al. ................ | 73/597 |
| 3,341,835 A | | 9/1967 | Werner et al. | |
| 3,926,271 A | | 12/1975 | Patashnick | |
| 3,970,146 A | | 7/1976 | Keenan, Jr. | |
| 4,092,858 A | * | 6/1978 | Edgerton ................ | 73/170.29 |
| 4,280,557 A | * | 7/1981 | Bodine ................... | 166/177.2 |
| 4,320,528 A | * | 3/1982 | Scharton et al. ............ | 376/310 |
| 4,444,146 A | * | 4/1984 | De Witz et al. ............ | 114/222 |
| 4,553,137 A | | 11/1985 | Marxer et al. | |
| 4,669,310 A | * | 6/1987 | Lester ........................ | 73/597 |
| 4,718,774 A | * | 1/1988 | Slough ........................ | 374/7 |
| 4,856,584 A | * | 8/1989 | Seidner ................ | 166/250.05 |
| 4,872,347 A | * | 10/1989 | Okabe et al. ................ | 73/634 |

(Continued)

FOREIGN PATENT DOCUMENTS

| | | |
|---|---|---|
| GB | 2 165 330 A | 10/1984 |
| GB | 2 351 810 B | 8/1999 |
| WO | 93/24199 | 6/1993 |

OTHER PUBLICATIONS

Allen, T.O. and Roberts, A.P., *Production Operations*, vol. 2, 2nd edition, pp. 11–19, OGCI, Tulsa, Ok. (1982).

Ref. 1, pp. 171–181. Allen, T.O. and Roberts, A.P., *Production Operations*, vol. 2, 2nd edition, OGCI, Tulsa, Ok. (1982).

Putnis, A, Putnis, C.V. and Paul, J.M., "The efficiency of a DTPA–based solvent in the dissolution of barium sulfate scale deposits", *SPIE International Symp. Oilfield Chemistry*, San Antonio, Texas, Feb. 1995, SPE 29094.

(Continued)

*Primary Examiner*—Hezron Williams
*Assistant Examiner*—Rose M. Miller
(74) *Attorney, Agent, or Firm*—William L. Wang; William B. Batzer; Dale Gaudier

(57) ABSTRACT

Described is a downhole apparatus for detecting and removing deposits from a surface exposed to wellbore fluids. The apparatus can monitor the rate of deposition and subsequently remove the deposited material. The combination of detection apparatus and removal apparatus provides a downhole instrument with self-cleaning operation mode.

29 Claims, 11 Drawing Sheets

U.S. PATENT DOCUMENTS

| | | | |
|---|---|---|---|
| 4,994,671 A | | 2/1991 | Safinya et al. |
| 5,038,033 A | * | 8/1991 | Carroll et al. ............... 250/256 |
| 5,072,388 A | * | 12/1991 | O'Sullivan et al. ............ 702/12 |
| 5,092,176 A | * | 3/1992 | Buttram et al. ................ 73/599 |
| 5,112,642 A | | 5/1992 | Wajid |
| 5,159,838 A | | 11/1992 | Lynnworth |
| 5,184,678 A | | 2/1993 | Pechkov et al. |
| 5,201,215 A | * | 4/1993 | Granstaff et al. ........... 73/54.41 |
| 5,591,922 A | | 1/1997 | Segeral et al. |
| 5,595,243 A | | 1/1997 | Maki, Jr. et al. |
| 5,646,338 A | | 7/1997 | Mercusot et al. |
| 5,661,233 A | * | 8/1997 | Spates et al. .............. 73/61.45 |
| 5,676,213 A | | 10/1997 | Auzerais et al. |
| 5,727,628 A | | 3/1998 | Patzner |
| 5,734,098 A | * | 3/1998 | Kraus et al. ............... 73/61.62 |
| 5,735,226 A | | 4/1998 | McNeal |
| 5,827,952 A | * | 10/1998 | Mansure et al. ........... 73/61.45 |
| 5,831,743 A | | 11/1998 | Ramos et al. |
| 5,889,209 A | | 3/1999 | Piedrahita et al. |
| 5,969,235 A | | 10/1999 | Allan |
| 6,131,659 A | * | 10/2000 | Johnson .................. 166/250.05 |
| 6,247,354 B1 | * | 6/2001 | Vig et al. ................... 73/54.41 |
| 6,286,370 B1 | * | 9/2001 | Sinha ........................... 73/579 |
| 2003/0101822 A1 | * | 6/2003 | Atherton ...................... 73/649 |

OTHER PUBLICATIONS

Jasinski, R, Taylor, K. and Fletcher, P., Taylor K, "Calcite scaling tendencies for North Sea HTHP wells: prediction, authentication and application", *SPE Symp. Oilfield Scale*, New Orleans, Louisiana, Sep. 1998.

Calange, S., Ruffier–Meray, V. and Behar, E., "Onset crystallization temperature and deposit amount for waxy crudes: experimental determination and thermodynamic modelling", *SPE International Symp. Oilfield Chemistry*, Houston, Texas, Feb. 1997, SPE 37239.

Gunarathne, G.P.P. and Keatch, R.W., "Novel techniques for monitoring and enhancing dissolution of mineral deposits in petroleum pipelines", *SPE Offshore Europe Conference*, Aberdeen, Sep. 1995, SPE 30418.

Gunarathne, G.P.P. and Keatch, R.W., "Novel techniques for monitoring and enhancing dissolution of mineral deposits in petroleum pipelines", *Ultrasonics*, 34, 411–419 (1996).

Martin, S.J., Granstaff, V.E. and Frye, G.C., "Characterisation of a quartz crystal microbalance with simultaneous mass and liquid loading", *Anal. Chem.*, 63, 2272–2281 (1991).

Sivaraman, A., Hu, Y., Thomas, F.B., Bennion, D.B. and Jamaluddin, A.K.M., "Acoustic resonance: an emerging technology to identify wax and asphaltene precipitation onset in reservoir fluids", *48th Annual Tech. Meet. The Petroleum Society*, Calgary, Canada, Jun. 8–11, 1997, paper CIM 97–96.

Jamaluddin, A.K.M., Sivaraman, A., Imer, D. Thomas, F.B. and Bennion, D.B., "A proactive approach to address solids (wax and asphaltene) precipitation during hydrocarbon production", *8th Abu Dhabi Intern. Petroleum Exhibit.*, Abu Dhabi, U.A.E., Oct. 11–14, 1998, SPE 49465.

Emmons, D.H. and Jordan, M.M., "The development of near–real time monitoring of scale deposition", *SPE Oilfield Scale Symposium*, Aberdeen, Jan. 27–28, 1999.

Emmons, D.H., Graham, G.C., Holt, S.P., and Jordan, M.M. "On–site, near–real–time monitoring of scale deposition", *SPE Annual Technical Conference and Exhibition*, Houston, Oct. 1999, SPE 56776.

Gabrielli, C., Keddam, M., Khalil, A., Maurin, G., Perrot, H., Rosset, R. and Zidoune, M., "Quartz crystal microbalance investigation of electrochemical calcium carbonate scaling", *J. Electrochem. Soc.*, 145, 2386–2395 (1998).

Nohata, Y. and Taguchi, H., "An ultrasensitive fouling monitoring system for cooling towers", *Materials Performance*, 34, 43–46 (1995).

Stock, D.D., "The use of pressure drop measurements to monitor scale build–up in pipelines and wells", *Geothermal Resources Council Trans.*, 14, 1645–1651 (1990).

Oilfield Production Analysts Ltd, Aberdeen: product brochures for P–MAC 2000, 3000 and 4000 series.

Flemming, H–C., Tamachkiarowa, A., Klahre, J. and Schmitt, J., "Monitoring of fouling and biofouling in technical systems", *Water Sci. Tech.*, 38, 291–298 (1998).

Esche, R., "Untersuchung der Schwingungkavitation in Flüssigkeiten", *Acustica*, 2, AB208–218 (1952).

Mason, T.J. and Lorimer, J.P., *Sonochemistry: Theory, Applications and Uses of Ultrasound in Chemistry*, p 31, Ellis Horwood, Chichester, UK (1988).

Gollapdi, U.K., Bang, S.S. and Islam, M.R., "Ultrasonic treatment for removal of asphaltene deposits during petroleum production", *SPE International Conf. Formation Damage Control*, Lafayette, Louisiana, Feb. 1994, SPE 27377.

Venkitaraman, A., Roberts, P.M. and Sharma. M.M., "Ultrasonic removal of near–wellbore damage caused by fines and mud solids", *SPE Drilling & Completions*, 10, 193–197 (1995).

Roberts, P.M., Venkitaraman, A. and Sharma, M.M., "Ultrasonic removal of organic deposits and polymer induced formation damage", *SPE Formation Damage Control Symp.*, Lafayette, Louisiana, Feb. 1996, SPE 31129.

Widener, M.W., "The development of high–efficiency narrow–band transducers and arrays", *J. Acoust. Soc. Amer.*, 67, 1051–7 (1980).

Widener, M.W., "The development of a deep submergence air–backed transducer", *J. Acoust. Soc. Amer.*, 80, 1852–3 (1986).

Lal, A. and White, R.M., "Silicon microfabricated horns for power ultrasonics", *Sensors and Actuators*, A54, 542–546 (1996).

* cited by examiner

DOWNHOLE DEPOSITION MONITORING SYSTEM

This invention relates to apparatus and methods for monitoring solid deposits of material in a wellbore and operating downhole sensors and other wellbore equipment. Particularly, the invention relates to such apparatus and methods for sensing and removing solid deposits in hydrocarbon wells.

BACKGROUND OF THE INVENTION

The formation of both organic and inorganic deposits in the near wellbore region of producing formations and on the tubing of a producing hydrocarbon well can be a major and costly problem. See, e.g. Allen, T. O. and Roberts, A. P., *Production Operations*, Vol. 2, 2nd edition, pp. 11–19 and 171–181, OGCI, Tulsa, Ok. (1982); Cowan, J. C and Weintritt, D. J., *Water-formed Scale Deposits*, Gulf Publishing Co., Houston (1976). The deposits can seriously impede the productivity of wells by reducing the near wellbore permeability of producing formations and progressively restrict the diameter of the tubing.

The formation of inorganic deposits, or scale, is caused by the precipitation of inorganic salts from produced water. Calcium carbonate scale is usually formed by the change in the pressure and temperature of the produced water in the near wellbore and in the production tubing. Barium, strontium and calcium sulphate scales are usually formed by the mixing of formation water and seawater injected into producing wells; the high concentration of sulphate in seawater mixes with the high concentrations of divalent cations in formation waters with the resulting precipitation of the sulphate salts. The formation of scale may be partly prevented by water shut-off treatments and the use of scale inhibitors. Once formed, scale can be removed only with some difficulty; calcium carbonate scale can be dissolved by mineral acids and barite scale can be removed by milling or scale dissolvers such as EDTA. See, e.g. Putnis, A, Putnis, C. V. and Paul, J. M., "The efficiency of a DTPA-based solvent in the dissolution of barium sulfate scale deposits", *SPE International Symp. Oilfield Chemistry*, San Antonio, Tex., February 1995, SPE 29094. In extreme cases the production tubing must be removed and replaced, although the presence of radioactive scale (due to the presence of radium salts) can make scale disposal an environmental issue.

The production of hydrocarbons frequently causes the precipitation of organic precipitates such as paraffin waxes and asphaltenes. These organic precipitates are caused by changes in the pressure and temperature of the produced fluids in the near wellbore. The precipitates can be removed with solvent washes, although the disposal of the solvent after cleaning represents an increasing environmental problem.

The solubility of various inorganic and organic species can be predicted from thermodynamic models of the electrolyte solutions or hydrocarbons. See, e.g. Jasinski, R, Taylor, K. and Fletcher, P., "Calcite scaling—North Sea HTHP wells", *SPE Symp. Oilfield Scale*, Aberdeen, January 1999; Calange, S., Ruffier-Meray, V. and Behar, E., "Onset crystallization temperature and deposit amount for waxy crudes: experimental determination and thermodynamic modelling", *SPE International Symp. Oilfield Chemistry*, Houston, Tex., February 1997, SPE 37239. However, thermodynamic models are essentially equilibrium models and they cannot predict any details of the precipitation process such as the location of precipitation, the rate of precipitation or the degree of supersaturation that the fluid can tolerate.

Several patents and papers have described both acoustic and non-acoustic methods for sensing the formation of scale in producing hydrocarbon wells and similar environments. An acoustic method for measuring the thickness of metal oxide corrosion products on the inside of boiler tubes has been described. See Lester, S. R., "High frequency ultrasonic technique for measuring oxide scale on the inner surface of boiler tubes", U.S. Pat. No. 4,669,310, Jun. 2, 1987. The thickness of oxide scale is determined by the time of flight of an acoustic pulse applied from the external surface of the pipe. The frequency of the acoustic pulse was 50 MHz, which enabled a scale thickness of approximately 0.1 mm to be detected. The use of an automated ultrasonic inspection system for determining the thickness of scale formation which has formed on the inside of heat transfer tubes in boilers has been described. See Okabe, Y., Iwamoto, K., Torichigai, M., Kaneko, S., Ichinari, J. and Koizumi, K., "Automated ultrasonic examination system for heat transfer tubes in a boiler", U.S. Pat. No. 4,872,347, Oct. 10, 1989. A rotating transducer was inserted into the tubes and their diameter as a function of location determined by the reflection of sound from the scale-water interface. An acoustic wireline logging tool, Schlumberger's Cement Evaluation Tool (CET), has been used to determine the accumulation of scale on the casing of geothermal wells. See, U.S. Pat. No. 5,072,388, to O'Sullivan et al. The interfaces between the scale and wellbore fluid and the scale and the casing are determined by the transit time of the acoustic waves, which have a frequency of approximately 0.5 MHz. U.S. Pat. No. 5,092,176 disclosed a method for determining the thickness of scale on the inside of a water pipe by the attenuation of acoustic energy emitted and received by a transducer on the outside of the pipe. The optimum frequency range for the ultrasound was observed to be 3–7 MHz. For example, measurements made using ultrasound below a frequency of 3 MHz gave poor sensitivity to scale thickness and beam spreading was observed to be a problem. An acoustic method of identifying scale types and scale thickness in oil pipelines using the attenuation in the reflected acoustic signal from a tool that is moved through the inside of the pipe has been described. See, Gunarathne, G. P. P. and Keatch, R. W., "Novel techniques for monitoring and enhancing dissolution of mineral deposits in petroleum pipelines", *SPE Offshore Europe Conference*, Aberdeen, September 1995, SPE 30418 (hereinafter "Gunarathne"); Gunarathne, G. P. P. and Keatch, R. W., "Novel techniques for monitoring and enhancing dissolution of mineral deposits in petroleum pipelines", *Ultrasonics*, 34, 411–419 (1996) (hereinafter "Gunarathne and Keatch"). The frequency of the ultrasound used was in the range 3.5–5.0 MHz, which allowed the thickness of barium sulphate scale on steel to be measured to an accuracy of ±0.5 mm.

U.S. Pat. No. 5,661,233 (hereinafter "Spates et al.") disclosed several acoustic-wave devices for determining the deposition of organic precipitates, such as paraffin wax, on to a sensing surface immersed in a petroleum-based fluid. The acoustic measurements were made with devices using various acoustic modes: surface acoustic waves and thickness shear, acoustic plate and flexural plate modes. The devices measured changes in the damping voltage and resonant frequency of the device as the wax precipitate formed, although no details were disclosed regarding the operating frequencies of the acoustic devices or the acoustic power they generated. Spates et al. discussed periodic cleaning of the sensing surface of the acoustic device by heating the surface to melt the paraffin wax. However, the use of acoustic energy to clean the organic precipitates from the acoustic sensor was not disclosed or suggested. Several applications of the measurement of wax accumulation were described, including location of acoustic devices on the sea floor to monitor the production of hydrocarbon from oil wells and guide well treatments. The application of a quartz microbalance to measure simultaneously mass loading and liquid properties has been described. See, U.S. Pat. No. 5,201,215; Martin, S. J., Granstaff, V. E. and Frye, G. C., "Characterisation of a quartz crystal microbalance with simultaneous mass and liquid loadings", Anal. Chem., 63, 2272–2281 (1991) (collectively hereinafter "Granstaff and Martin"). The authors used changes in the resonant frequency and magnitude of the maximum admittance of a quartz microbalance to differentiate between changes in the mass of material deposited from a liquid and changes in the properties of the liquid (density and viscosity). The operating frequency of the quartz microbalance was close to 5 MHz, at which value the resonator was able to detect solid films of the order of 0.1 $\mu$m in thickness.

The application of an on-line quartz crystal microbalance to monitor and control the formation of organic and inorganic precipitates from hydrocarbons and water has been described. See, U.S. Pat. No. 5,734,098 (hereinafter "Kraus et al."). The quartz crystal microbalance consisted of a thickness-shear mode resonator and was described by Kraus et al. as being substantially similar to those disclosed by Granstaff and Martin. Kraus et al. described the use of the thickness-shear mode resonator for the on-line measurement of scaling, corrosion and biofouling in industrial processes. They also described the use of the measurement of deposit formation to determine the treatment required to correct the industrial process and prevent continual deposit formation, e.g., by use of a chemical additive such as an inorganic scale inhibitor. Although Kraus et al. described the use of a thickness-shear mode resonator to monitor deposit formation from hydrocarbons, industrial water and their mixtures (including emulsions), no disclosure or suggestion was made to the operation of these sensors in or near producing hydrocarbon wells, on either a temporary or permanent basis. Additionally, there was no disclosure or suggestion regarding the treatment of producing hydrocarbon wells, for either organic or inorganic deposit formation, on the basis of measurements made by these sensors.

A laboratory acoustic resonance technique to determine the onset of the precipitation of wax and asphaltene from produced hydrocarbons has been described. See, Sivaraman, A., Hu, Y., Thomas, F. B., Bennion, D. B. and Jamaluddin, A. K. M., "Acoustic resonance: an emerging technology to identify wax and asphaltene precipitation onset in reservoir fluids", 48th Annual Tech. Meet. The Petroleum Society, Calgary, Canada, Jun. 8–11, 1997, paper CIM 97–96; Jamaluddin, A. K. M., Sivaraman, A., Imer, D. Thomas, F. B. and Bennion, D. B., "A proactive approach to address solids (wax and asphaltene) precipitation during hydrocarbon production", 8th Abu Dhabi Intern. Petroleum Exhibit., Abu Dhabi, U. A. E., 11–14 Oct. 1998, SPE 49465. The spectrum of resonant frequencies of a sample of liquid hydrocarbon in a cylinder of fixed length and cross-sectional area was obtained as a function of temperature and pressure. The resonant spectra were collected using two ultrasonic transducers operating over the frequency range 0–40 kHz, although significant resonances were observed only over the frequency range 5–35 kHz. The precipitation of wax and/or asphaltene from the liquid hydrocarbon sample as the pressure and temperature of the sample was changes resulted in changes in the frequency of the resonances and changes in their amplitude. The changes in the resonant spectra were attributed to changes velocity of sound in the liquid. No reference was made to the precipitation of wax or asphaltene on the transmitting or receiving transducer.

The use of a thickness-shear mode resonator to monitor the formation of barium sulphate in samples of produced water collected at the well head has been described. See, Emmons, D. H. and Jordan, M. M., "The development of near-real time monitoring of scale deposition", SPE Oilfield Scale Symposium, Aberdeen, 27–28 Jan. 1999 (hereinafter "Emmons and Jordan"). The resonator was immersed in a fixed volume of produced water and known amounts of soluble barium ions were added to precipitate barium sulphate scale. The resonator detected the formation of scale on its sensing surface by a decrease in resonant frequency. The amount of barium added before scale formation was detected by the resonator gave an indication of the level of inhibition in the produced water. Emmons and Jordan argued that the formation of scale by small additions of barium ions indicated the produced water was close to scaling and treatment of the well by a suitable scale inhibitor was required. Note that this method of monitoring scale formation is not an in situ method and does not measure the spontaneous formation of scale under downhole conditions of temperature, pressure, composition and flow. In addition, the resonator was not able to clean the scale from its sensing surface. A quartz crystal microbalance to monitor the formation of calcium carbonate scale under laboratory conditions has been described. See, Gabrielli, C., Keddam, M., Khalil, A., Maurin, G., Perrot, H., Rosset, R. and Zidoune, M., "Quartz crystal microbalance investigation of electrochemical calcium carbonate scaling", J. Electrochem. Soc., 145, 2386–2395 (1998). The resonant frequency of the microbalance was 6 MHz and calcium carbonate deposition rates of 200–400 $\mu$g/cm$^2$ per hour were measured. The calcium carbonate scale was observed to be the mineral calcite, which, with an assumed density of 2.71 g/cm$^3$, gave deposits of 0.7–1.5 $\mu$m in thickness. The rate of scale accumulation measured by the quartz microbalance was compared with a standard electrochemical scale monitor that measured the redox current passing through an electrode as water was reduced. The decline in redox current gave an indirect measure of the decrease in the surface area of the electrode as it was covered with scale and was observed to be less sensitive to scale formation than the quartz crystal microbalance. The use of a piezoelectric quartz crystal to monitor the fouling of surfaces in a water cooling tower by inorganic scale and bacterial growth at ambient conditions has been described. See, Nohata, Y. and Taguchi, H., "An ultrasensitive fouling monitoring system for cooling tower", Materials Performance, 34, 43–46 (1995) (hereinafter "Nohata and Taguchi"). Although Nohata and Taguchi did not specifically disclose the operating frequency of the quartz crystal, a value of about 5 MHz can be deduced from the measured accumulation rates of 1–20 $\mu$g/cm$^2$ per day.

The use of a tuning fork for measuring the deposition of scale in a surface process system has been disclosed. See, U.S. Pat. No. 5,969,235. The accumulation of scale on the tines of the tuning fork causes a shift in the characteristic vibrating frequency of the tuning fork as measured by a suitable electronic device, such as a piezoelectric cell. The change in vibrating frequency of the tuning fork, indicating the deposition of scale, was used to control the addition of scale inhibitor to the process stream.

Non-acoustic scale sensing techniques have also been reported. A method of determining the accumulation of scale in petroleum pipelines using a heat transfer sensor has been described. See, U.S. Pat. No. 4,718,774. The scale formed on the external wall of the sensor impeded the loss of heat from a heating element in the sensor to the fluid flowing in the pipeline. The decrease in heat flow was measured by means of a temperature sensor. A wellbore scale monitor that measured the radioactivity of the radium salts precipitated with other alkaline earth metal salts has been described. See, U.S. Pat. No. 4,856,584 (hereinafter "Sneider"). Sneider discloses the use of measurements of scale radioactivity to indicate when and where the placement of scale inhibitor is required. Another scale monitoring technique is disclosed in U.S. Pat. No. 5,038,033; the radioactivity of the scale was detected by a wireline gamma ray detector, correcting for the natural gamma radiation emitted from the surrounding rock formations.

Accurately measured pressure drops over various sections of a reinjection pipeline in a geothermal power plant has been used to monitor the growth of silica scale. See, Stock, D. D., "The use of pressure drop measurements to monitor scale build-up in pipelines and wells", *Geothermal Resources Council Trans.*, 14, 1645–1651 (1990). The measured pressure drops across the sections of pipe produced friction factors in the range 0.1–0.2, compared to an expected value of 0.01. Cleaning the silica scale from the pipeline sections using a wire brush pig resulted in the friction factor dropping below a value of 0.06. Both laboratory and field systems to evaluate the scaling potential of oilfield brine samples by monitoring the pressure drop across a capillary tube through which the brine flows and deposits scale are being currently produced by the company Oilfield Production Analysts Ltd. (see product brochures for P-MAC 2000, 3000 and 4000 series). Three optical techniques to monitor fouling in industrial process systems were described in Flemming, H-C., Tamachkiarowa, A., Klahre, J. and Schmitt, J., "Monitoring of fouling and biofouling in technical systems", *Water Sci. Tech.*, 38, 291–298 (1998). The techniques consisted of measurement of the intensity of light reflected from a small optical fibre probe, the measurement of turbidity through optical windows in a flow line (using periodically cleaned windows in the flow line as a reference optical pathlength) and an infrared spectroscopy flow cell. The accumulation of deposits and the chemical nature of the deposits on the optical windows of the infrared flow cell could be determined from the infrared spectra.

A number of published reports have described the application of sonic energy for cleaning producing oil wells and equipment in similar industrial processes. A method of cleaning downhole deposits, such as tar, from producing formations and production tubing was disclosed in U.S. Pat. No. 3,970,146. However, no details were given of the power or frequency of the sound used for wellbore cleaning. A low frequency (20–100 Hz) vibrating device for cleaning deposits on the walls of casing and tubing and in formations and gravel packs was disclosed in U.S. Pat. No. 4,280,557. The vibrations were generated in the device by an orbiting mass on an unbalanced rotor, which, in turn, produced a whirling vibratory pressure of large amplitude in the fluid in the annulus. U.S. Pat. No. 4,320,528 disclosed a method of removing iron oxide corrosion products and other scaling deposits from the pipes of steam generators using a combination of high power sound and a high-temperature solvent (e.g., sodium EDTA, citric acid and a corrosion inhibitor). The acoustic transducers operated in the frequency range 2–200 kHz and generated an output acoustic power greater than 0.2 W/cm$^2$, a value which is above the cavitation threshold of aerated water at ambient pressure and temperature. See, Esche, R., "Untersuchung der Schwingungkavitation in Flüssigkeiten", *Acustica*, 2, AB208–218 (1952); Mason, T. J. and Lorimer, *J. P., Sonochemistry: Theory, Applications and Uses of Ultrasound in Chemistry*, p 31, Ellis Horwood, Chichester, UK (1988). The transducers were located permanently on the outside of the heat exchanger tubes. U.S. Pat. No. 4,444,146 disclosed an ultrasonic method to clean the fouled surfaces of submerged structures, such as the hulls of ships. The ultrasonic cleaner consisted of two ultrasonic transducers focussed on a small area of surface to be cleaned. The transducers operated at slightly different frequencies, typically in the range 180–210 kHz; no details were disclosed on the acoustic power required to clean the fouled surfaces. UK Patent Application 2 165 330 A (hereinafter "D'Arcy et al.") disclosed a method of cleaning underwater structures to depths of up to 1000 meters using focussed ultrasound in the frequency range 40–100 kHz. The ultrasound was generated and focussed using an array of transducers located on the concave surface of a spherical cap. The density of acoustic power at the focal point of the array of transducers was stated to be about 500 W/cm$^2$, a value that is approximately 3 orders of magnitude above the cavitation threshold of water at ambient pressure. D'Arcy et al. suggested the high power acoustic array could be used to clean the base of oil production platforms. U.S. Pat. No. 5,184,678 disclosed the design of a high power acoustic logging tool to stimulate fluid production from oil wells. The acoustic power was provided by pulsed magnetostrictive transducers operating in the frequency range 5–30 kHz and emitting an acoustic power density of up to 1 W/cm$^2$. The tool was designed to give a stand-off from the treated formation of 0.2–0.5$\lambda$, where $\lambda$ is the wavelength of the sound in the borehole fluid. The treated formations were exposed to the acoustic power for periods of 5–60 minutes. According to U.S. Pat. No. 5,184,678, the applied ultrasound reduced the viscosity of the fluid in permeable formations and fluidised the particulate matter, thus facilitating its removal.

It has been shown that ultrasound applied at a frequency of 10 kHz could remove asphaltene deposits from a sand pack saturated with both water and kerosene at ambient pressure. See, Gollapdi, U. K., Bang, S. S. and Islam, M. R., "Ultrasonic treatment for removal of asphaltene deposits during petroleum production", *SPE International Conf. Formation Damage Control*, Lafayette, La., February 1994, SPE 27377. Although the acoustic power applied to the sand packs during cleaning was not measured, the ultrasonic transducer could generate a maximum output acoustical power of 250 W. The authors discussed the role of acoustic cavitation in the cleaning process and acoustic cavitation was undoubtedly achieved at the power settings reported. The asphaltene deposits were observed to be removed significantly more efficiently by the ultrasound in kerosene than in water. It has been demonstrated under laboratory conditions that the damage caused to permeable formation by the invasion of clay particles from drilling fluids can be partially removed by the application of high power ultrasound. See, Venkitaraman, A., Roberts, P. M. and Sharma. M. M., "Ultrasonic removal of near-wellbore damage caused by fines and mud solids", *SPE Drilling & Completions*, 10, 193–197 (1995). Two ultrasonic transducers were used; one was a high power ultrasonic horn operating at a frequency of 20 kHz with an output power of up to 250 W and the other was a low power transducer operating over frequency range 10–100 kHz. The same authors subsequently evaluated the application of high power ultrasound under laboratory conditions for the removal of organic deposits and formation damage caused by the invasion of drilling fluid filtrate containing water-soluble polymers. See, Roberts, P. M., Venkitaraman, A. and Sharma, N. M., "Ultrasonic removal of organic deposits and polymer induced formation damage", *SPE Formation Damage Control Symp.*, Lafayette, La., February 1996, SPE 31129. Using the same ultrasonic transducers, it was demonstrated that polymer-induced formation damage was considerably more difficult to remove than the damage caused by clay fines. However, formation damage resulting from the precipitation of wax in the test core samples could be removed by sonication when the core samples were soaked in a suitable solvent.

U.S. Pat. No. 5,595,243 disclosed the use of a general purpose acoustic cleaning tool for improving the near wellbore permeability of producing formations by redissolving or resuspending restricting materials. The cleaning tool was reported to generate acoustic power densities of up to 2 $W/cm^2$, which is above the cavitation threshold for water at ambient temperature and pressure. See, U.S. Pat. No. 4,280, 557. The tool, which consisted of an array of air-backed high power acoustic transducers of the type described by Widener, was designed to be deployed into the well on a wireline cable. See, Widener, M. W., "The development of high-efficiency narrow-band transducers and arrays", *J. Acoust. Soc. Amer.*, 67, 1051–7 (1980); Widener, M. W., "The development of a deep submergence air-backed transducer", *J. Acoust. Soc. Amer.*, 80, 1852–3 (1986). The transducers described by Widener would be expected to operate in the frequency range 10–100 kHz. U.S. Pat. No. 5,676,213 disclosed the use of high power ultrasound to remove the filter cake formed by the drilling fluid during the drilling of a well in order to measure the pressure in permeable formations. The high power ultrasound was generated by a focussing transducer operating in the frequency range 100–500 kHz and capable of operating at a peak input power of up to 1 kW. U.S. Pat. No. 5,727,628 disclosed an ultrasonic tool for cleaning producing wells. The wireline-deployable tool consisted of an array of magnetostrictive transducers operating in the frequency range 18–25 kHz (preferably at 20 kHz) and emitting an acoustic power density in the range 8–12 $W/cm^2$. The tool was also equipped with a pump to remove the debris of the fouling deposits disaggregated by the ultrasonic tool. U.S. Pat. No. 5,735,226 disclosed a method to prevent the fouling of ships and other marine structures by the use of ultrasound over the frequency range 20–60 kHz. One demonstration of the technique was the location of a number of ultrasonic transducers on the hull of a ship over a period of 4 months. Over this time period the transducers, which were powered intermittently, gave effective relief from marine fouling. U.S. Pat. No. 5,735,226 revealed no details of the power consumption of the transducers, but one embodiment of the invention consisted of the array being powered by a 9 volt battery. U.S. Pat. No. 5,889,209 disclosed the use of high power ultrasound to prevent biofouling of chemical sensors used in aquatic environments. The ultrasound was generated by a transducer operating in the frequency range 10–100 kHz and yielding a sufficient power density (>0.1–1 $W/cm^2$) to drive acoustic cavitation. U.S. Pat. No. 5,889,209 disclosed the use of the acoustic cleaning technique to maintain the performance of a dissolved oxygen sensor located in microbiologically active water for seven days. The transducer was located over the range 4–10 mm from the active membrane of the oxygen sensor and activated for a time period of 6–90 seconds over a time interval of 5–120 minutes.

Several papers and patents have reported on the use of high power ultrasound to accelerate the dissolution of scale by chemical scale dissolvers applied in pipelines and producing oil wells. Paul, J. M. and Morris, R. L., "Method for removing alkaline scale", International Patent Application WO 93/24199, 9 Dec. 1993 describes the use of low frequency (1.5–6.5 kHz) sonic energy to accelerate the dissolution of alkaline earth metal scales using scale dissolving solutions (typically containing the chelating agents EDTA or DTPA). Gunarathne, and Gunarathne and Keatch have shown that the application of low-power ultrasound can increase the rate of dissolution of barium sulphate scale using commercially available scale dissolvers; the power density was claimed to be below that required to cavitate the scale dissolving solution.

In conclusion, there appears to be no prior art that teaches or suggests either an acoustic scale sensor or an acoustic cleaning device located permanently or quasi-permanently in a well producing hydrocarbons. There appears to be no prior art of teaches or suggests the concept of a sensor for hydrocarbon wells to monitor the formation of inorganic or organic scales, biofouling or corrosion and initiate a cleaning action. Additionally, there appears to be no prior art that teaches or suggests an on-line deposits monitoring and cleaning device located on the surface facilities of a producing oil well using an ultrasonic transducer operating in its longitudinal mode and coupled to the produced fluids using a coupling material, such as an acoustic horn, to which the deposits adhere.

SUMMARY OF THE INVENTION

It is an object of this invention to describe an apparatus that can be placed at various locations to monitor the deposition of scale and other deposits and preferably to remove such deposits.

According to the invention a deposit monitoring apparatus located in a hydrocarbon wellbore is provided comprising: an acoustic device adapted to operate in a resonance mode including a monitoring surface directly exposed to fluids in a hydrocarbon wellbore, wherein the deposition of material on the monitoring surface is monitored by measuring a change in resonance frequency of the acoustic device; and a power supply adapted to supply said monitor with electrical energy.

The acoustic device is preferably mounted either permanently or quasi-permanently in the wellbore.

According to another aspect of the invention, a deposit monitoring apparatus located in a hydrocarbon wellbore is provided, comprising: a deposit monitor adapted to measure deposition of material on a monitoring surface that is directly exposed to fluids in the hydrocarbon wellbore; a power supply adapted to supply said monitor with electrical energy; and a deposit removal system in communication with the deposit monitor adapted to at least partially remove the deposition from the monitoring surface, the deposit removal system being in a control loop with said deposit monitor.

In a preferred embodiment the deposit monitor is a high power ultrasonic transducer, operating in a longitudinal mode, coupled to the fluids produced from the well by a solid coupling device, such as an acoustic horn, for measuring the deposition of the organic and inorganic scales that form from the fluids produced in hydrocarbon wells. By longitudinal mode we mean that the surface of the device exposed to the fluid is move predominantly normal rather than parallel to the exposed surface.

The transducer is preferably designed to operate in the frequency range 10–250 kHz with a maximum acoustical power output of 10–500 W. The maximum power is preferably only used during the cleaning process for less than 10 seconds or even less than 1 second. More preferably the frequency range is between 10 kHz and 150 kHz. The optimal frequency range is believed to lie within the range of 50 to 100 kHz. It was found that higher frequencies, particularly frequencies in the MHz region, are not applicable for permanent downhole deployment.

The growth of wellbore deposits is monitored by the decrease in the resonant frequency of the transducer with increasing thickness of deposit. The resonant frequency is conveniently determined from the real part of the admittance spectrum of the transducer. The horn amplifies the effect of the scale deposit on the measured admittance of the transducer.

The term "horn" is used as a generic expression for a solid coupling device, sally consisting of a tapering end piece mounted onto the body of the acoustic transducer. The horn can be bolted or glued to the body of the transducer material. The length of the horn is preferably some integer multiple of half the wavelength of the acoustic wave generated. The tapering can be achieved by cutting steps into the material or smoothly, e.g., as exponential tapering.

The horn material can be chosen arbitrarily from a large variety of solid materials. It is however a preferred feature of the invention to have the horn tip made of a material that matches the properties of the surrounding material, so as to ensure that the deposits on the surrounding material are accurately measured.

At least the tip of the horn is directly exposed to the wellbore fluid causing the deposition.

The transducer is able to detect inorganic deposits or scales, such as barium sulphate or calcium and organic deposits, such as waxes, at a thickness of approximately 100 $\mu$m.

Scales can be removed from the transducer by operation at high power; the transducer is therefore able both to detect and clean deposits. The ultrasonic transducer is also able to clean scale from the surfaces of other components located at various positions in producing hydrocarbon wells, such as those made of glass, metal or plastics. The acoustic transducers can be permanently located in producing hydrocarbon wells and indicate the location and rate of scale deposition. The measurement of scale deposition can be used to direct scale treatment procedures, such as the placement of inhibitors or the application of scale dissolvers, and to warn of scale accumulation on critical downhole production equipment, such as chokes, sliding sleeves and separators. The acoustic scale sensor can also be used to determine the effectiveness of any treatment to remove scale or other wellbore deposits.

The control loop comprises either be a suitably programmed microprocessor or computer executing preprogrammed tasks. Or, it could include visual display units allowing a human operator to make decisions based on the measurements provided by the deposit monitor.

Permanently or quasi-permanently installed in a wellbore or below the surface of the Earth refers to installation that are fixed to the wellbore and thus can be retrieved to the surface only under great costs and even sacrifice of equipment.

These and other features of the invention, preferred embodiments and variants thereof, possible applications and advantages will become appreciated and understood by those skilled in the art from the following detailed description and drawings.

DRAWINGS

FIGS. 1A–D are schematic illustrations of examples of acoustic devices, according to certain embodiments of the invention;

Figure 9A:
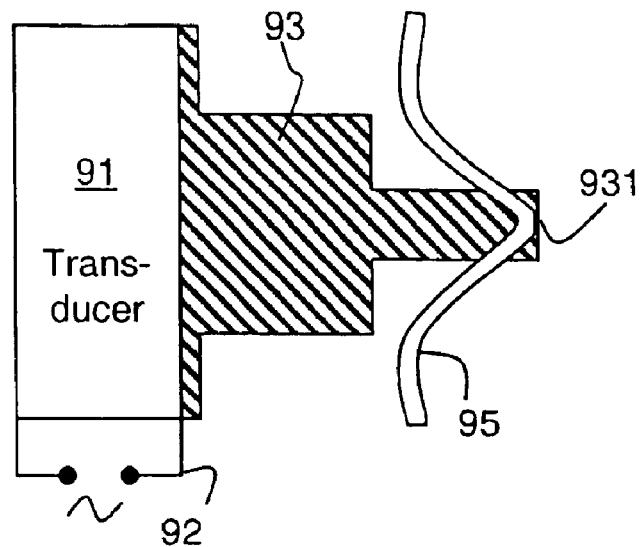
Figure 10:
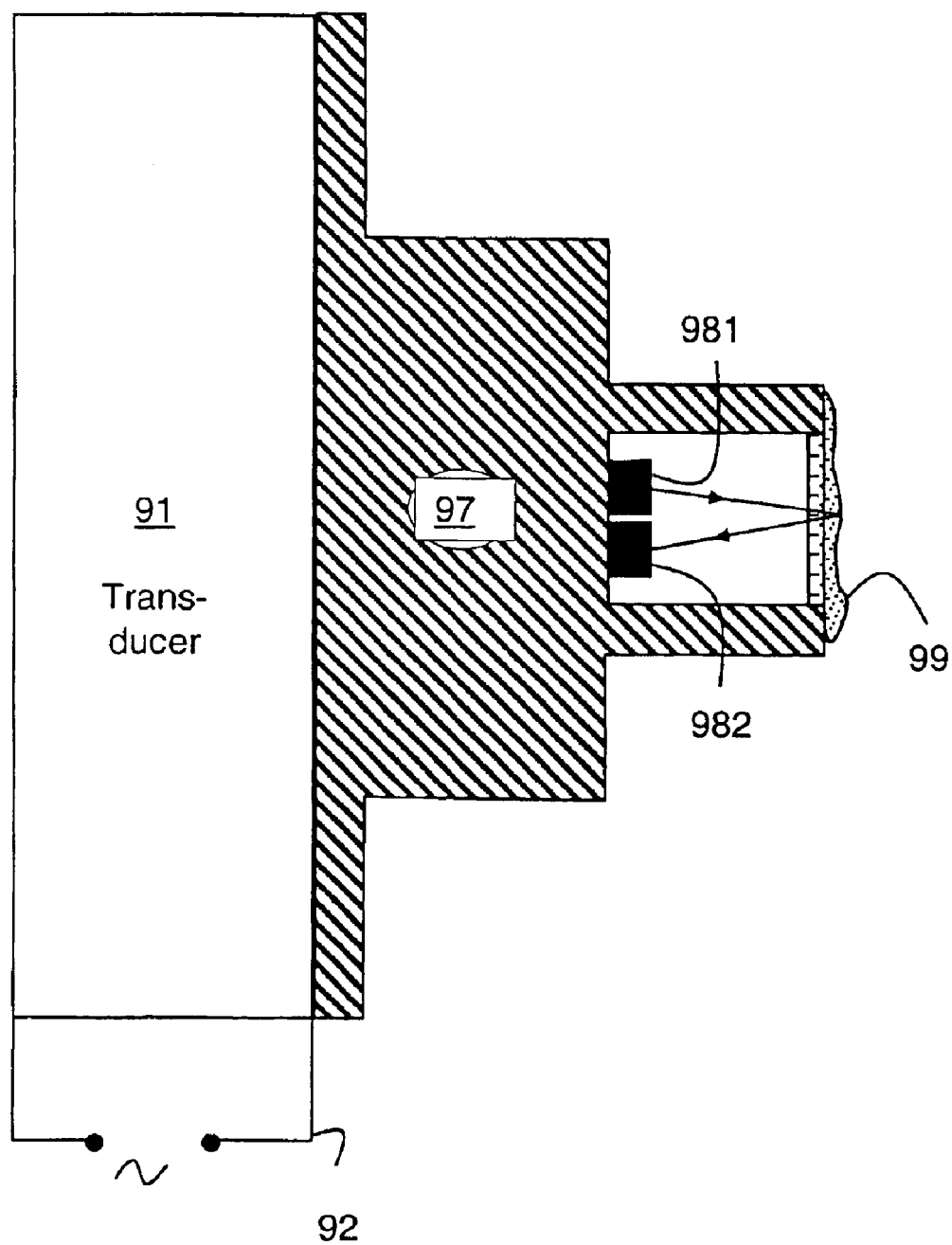

FIGS. 9A,B illustrate further sensor installations with self-cleaning equipment in accordance with the invention; and FIG. 10 shows a schematic sensor adapted to further analyse wellbore deposits.

MODE(S) FOR CARRYING OUT THE INVENTION (I) Acoustic Scale/Deposits Sensor

The scale (or deposits) sensor consists of an ultrasonic piezoelectric transducer operating in a longitudinal mode coupled to a suitable metal horn. The resulting ultrasonic device is characterised by a sharp resonant frequency, which can be conveniently determined by the measurement of the admittance (or impedance) spectrum of the device. The resonance frequency of the appropriate longitudinal mode is sensitive to any solid deposit that forms on the tip of the horn and the magnitude of the frequency shift is a measure of the mass loading. These ultrasonic transducers typically operate in the frequency range 10–100 kHz and can deliver high levels of acoustic power, typically in the range 1–500 W, when driven by a high input alternating voltage at its resonant frequency.

FIG. 1 shows schematics of several types of acoustic horn attached to an ultrasonic transducer. The basic elements of the scale deposit sensor 10 are a transducer 11 made of piezoelectric material, a power supply with electrodes 12 to cause oscillations of the transducer, and a horn 13. The horn is made of aluminum. The working surface of the transducer 131, on which the deposition of the scale is sensed, is the tip of the horn. In a downhole and surface installations, the tip 131 (or 141, 151, and 161 for the embodiments of FIGS. 1B, 1C, and 1D respectively) will be exposed to wellbore/production fluids and accumulate deposits.

The resonant frequency of the acoustic device operating in a longitudinal mode is determined by the size of the piezoelectric and the attached horn and the materials from which the piezoelectric and metal horn are constructed. The variants differ in their respective horn design. The horn 13 shown in FIG. 1A has a stepwise tapering. In FIG. 1B, the tapering is smooth with an exponentially reducing diameter of the horn 14. The horn coupled to the ultrasonic piezoelectric transducer is made of aluminium. The resulting device has a sharp resonant frequency in air of 40 kHz nominally and the area of the horn tip was 0.2 cm². In FIG. 1C, the tapering is degenerated to a single step giving the horn 15 a pin-like shape. Other horn shapes can be envisaged, including the case where its thickness is very much less than the wavelength of sound and the horn is a thin layer of material that couples the ultrasonic transducer to the bore hole fluids and their deposits.

Further indicated in FIG. 1 is the length of the horn as integer multiple N of half the wavelength ($\lambda/2$) of the acoustic wave generated by the transducer. FIG. 1D shows the case where the length of the horn 16 is very much less than $\lambda/2$ and the horn tip 161 has the same area as the ultrasonic transducer.

Figure 1A:
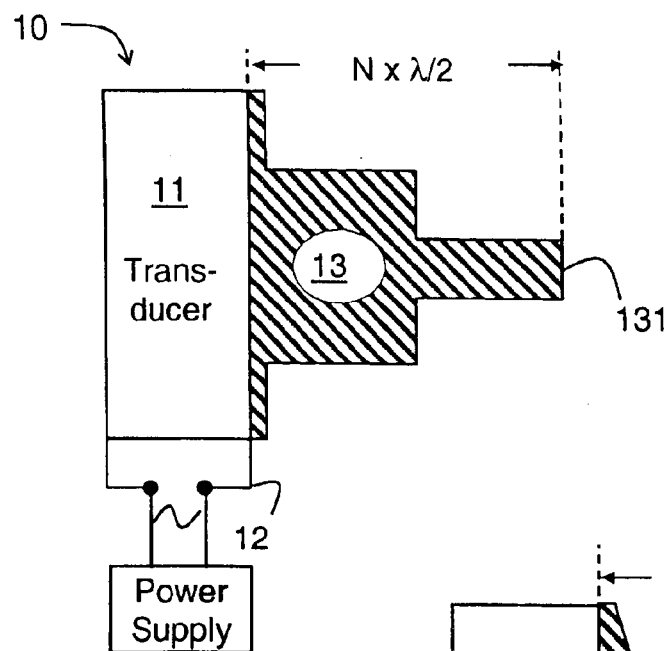
Figure 1B:
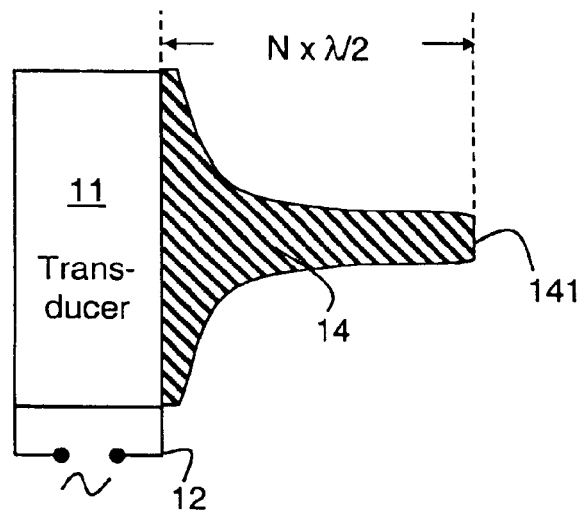
Figure 1C:
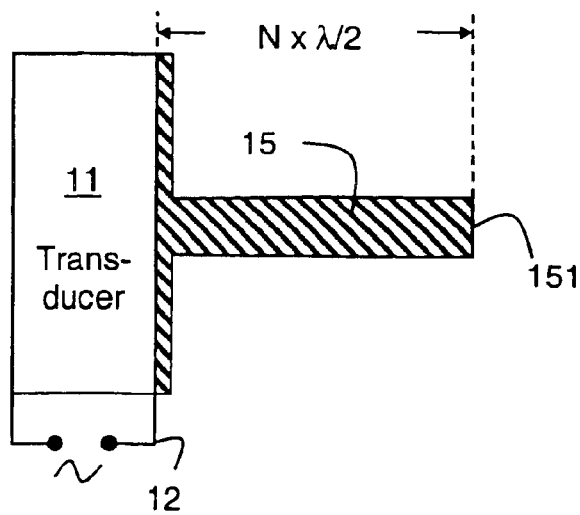
Figure 1D:
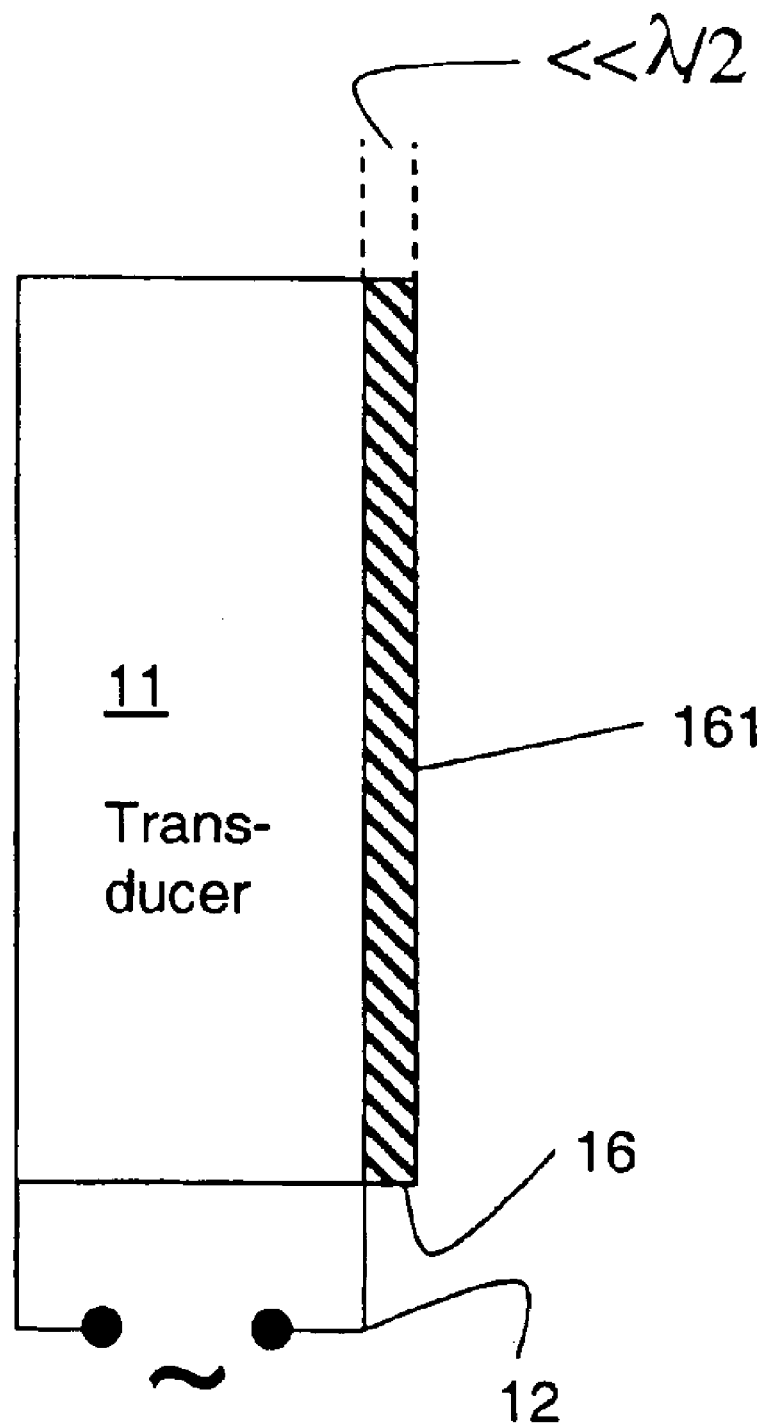

Table 1 shows the resonant frequency of the ultrasonic horns and the widths of the resonance at half peak height shown in FIG. 1A–C. The peak width of the resonance is typically 1–2% of the resonant frequency.

TABLE 1

Resonant frequencies in air of the ultrasonic transducers shown in FIG. 1A–C.

| Transducer type in FIG. 1 | Resonant frequency (kHz) | Width of resonace at half peak height (Hz) |
|---|---|---|
| A | 19.86 | 21 |
| B | 39.04 | 52 |
| C | 54.63 | 96 |

Figure 2A:
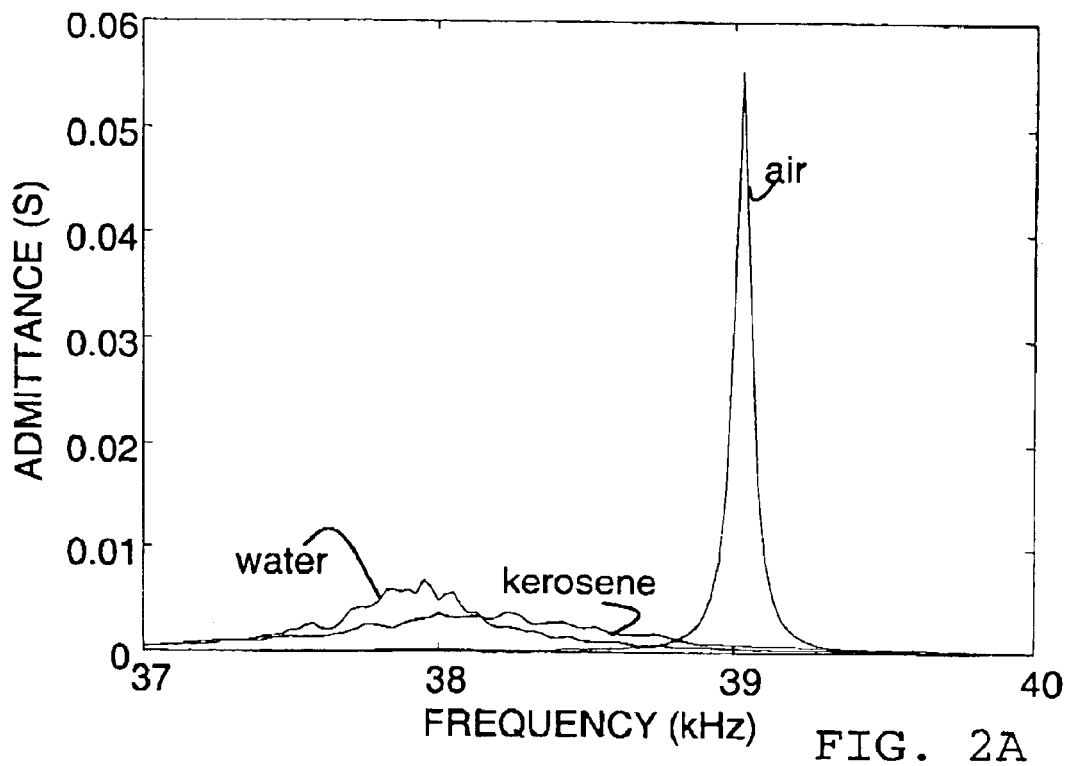
FIG. 2A shows the resonant frequencies of an acoustic device shown in FIG. 1B as measured by the real part of the admittance in air, water and kerosene.
Figure 2B:
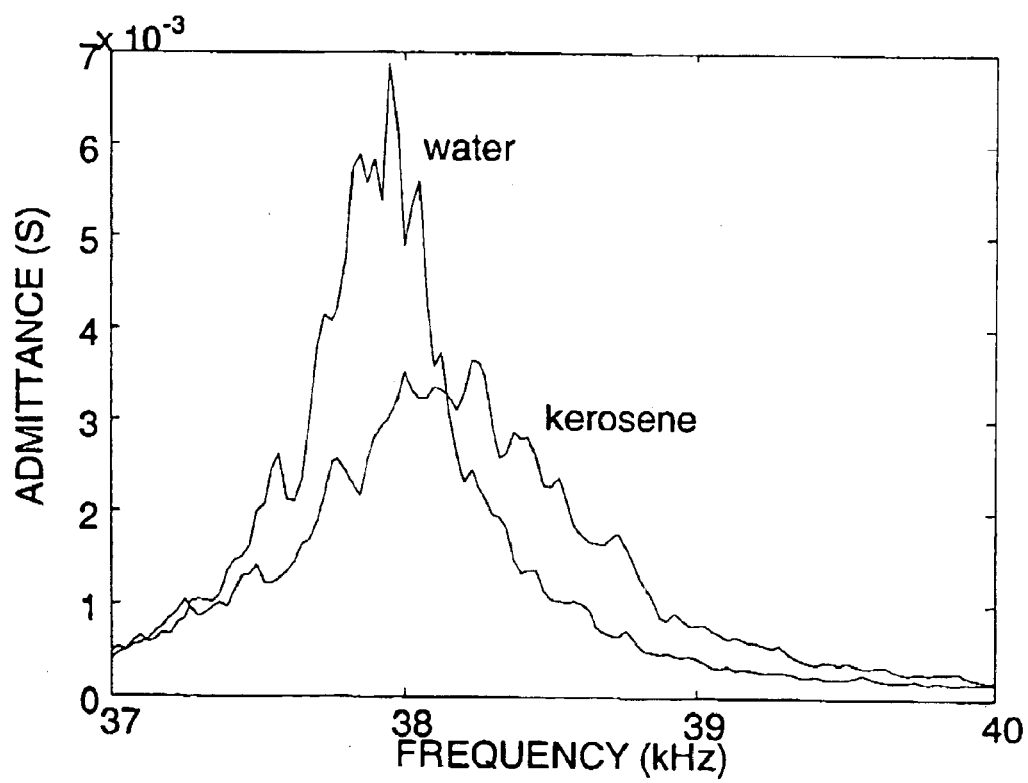
FIG. 2B shows an enlarged part of FIG. 2B.

FIG. 2 shows the resonant frequency of the acoustic sensor shown in FIG. 1B as measured by the real part of the admittance in Siemens (S). The resonant frequency of the ultrasonic transducer is modified by the nature of the fluid in which it is immersed. FIG. 2 compares the resonant frequency of the ultrasonic transducer immersed in air, water and kerosene. The resonance frequency of the transducer decreases when the metal horn is immersed in a denser fluid and the resonance broadens with more viscous fluids. The fine structure (shown in FIG. 2B) on the admittance spectra measured when the transducer is immersed in water and kerosene at ambient pressure is caused by the attachment of small air bubbles to the horn.

Figure 3:
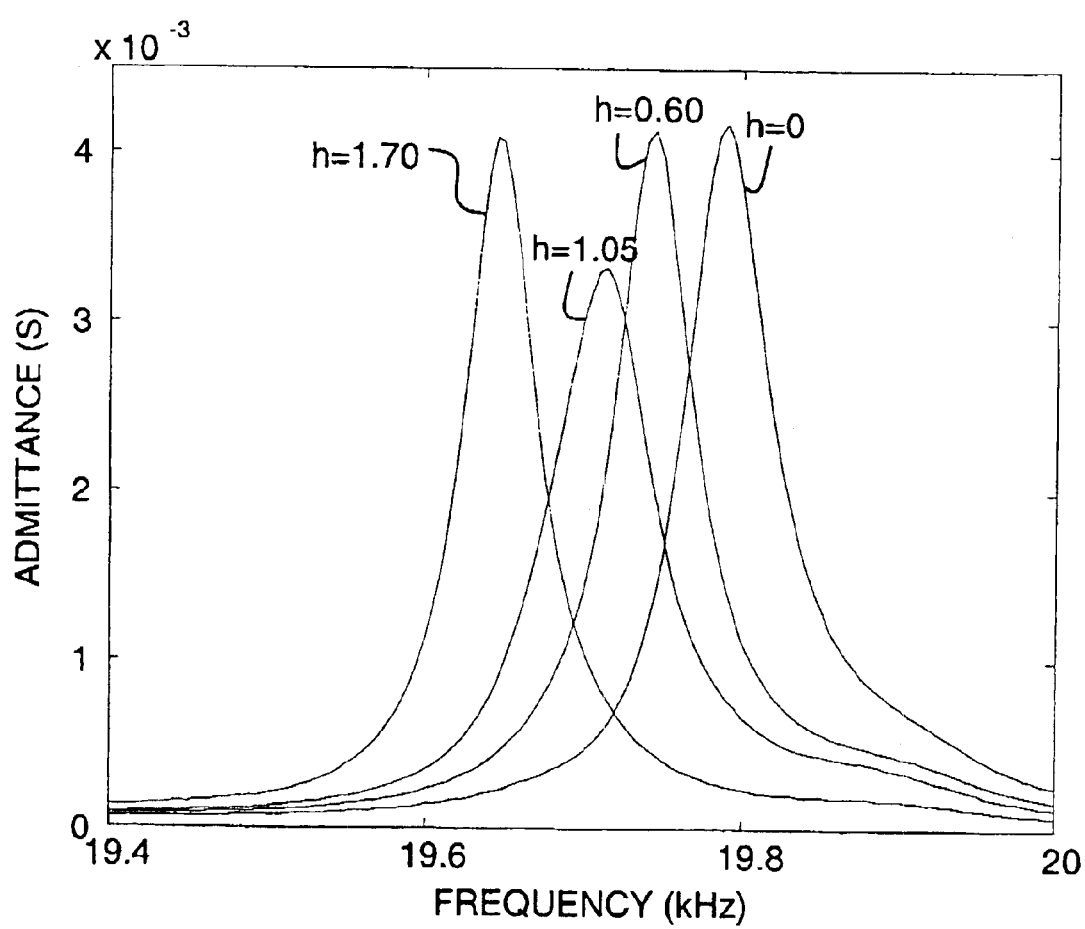
FIG. 3 illustrates the shift of the resonant frequency with increasing scale deposition at a hydrostatic pressure of 272 bar (4000 psi)

FIG. 3 shows the shift in the resonant frequency of a transducer and metal horn with thickness of attached scale when the horn is immersed in water in a pressure vessel at a hydrostatic pressure of 4000 psi (270 bar). The resonant frequency of the 20 kHz transducer shifts by 85 Hz per millimeter of scale of density 4.50 g/cm³.

Further measurements show the variation of the shift in the resonance frequency of a 40 kHz transducer as a function of scale thickness in water at ambient pressure for two scale types with densities of 2.75 and 4.50 g/cm³. The resonant frequency of the transducer decreases by 774 Hz per millimeter of scale of density $\rho=2.75$ g/cm³ and 966 Hz per millimeter of scale of density $\rho=4.50$ g/cm³.

The accumulation of inorganic scale can also be detected by a shift in the resonant frequency of a transducer when the horn is immersed in a liquid hydrocarbon. When comparing the admittance spectra of a 40 kHz transducer and horn immersed in kerosene at ambient pressure with and without inorganic scale attached, it was found that the shift in the resonant frequency of the transducer is 1317 Hz per millimeter of scale of density $\rho=4.50$ g/cm³ in kerosene at ambient pressure.

Figure 4:
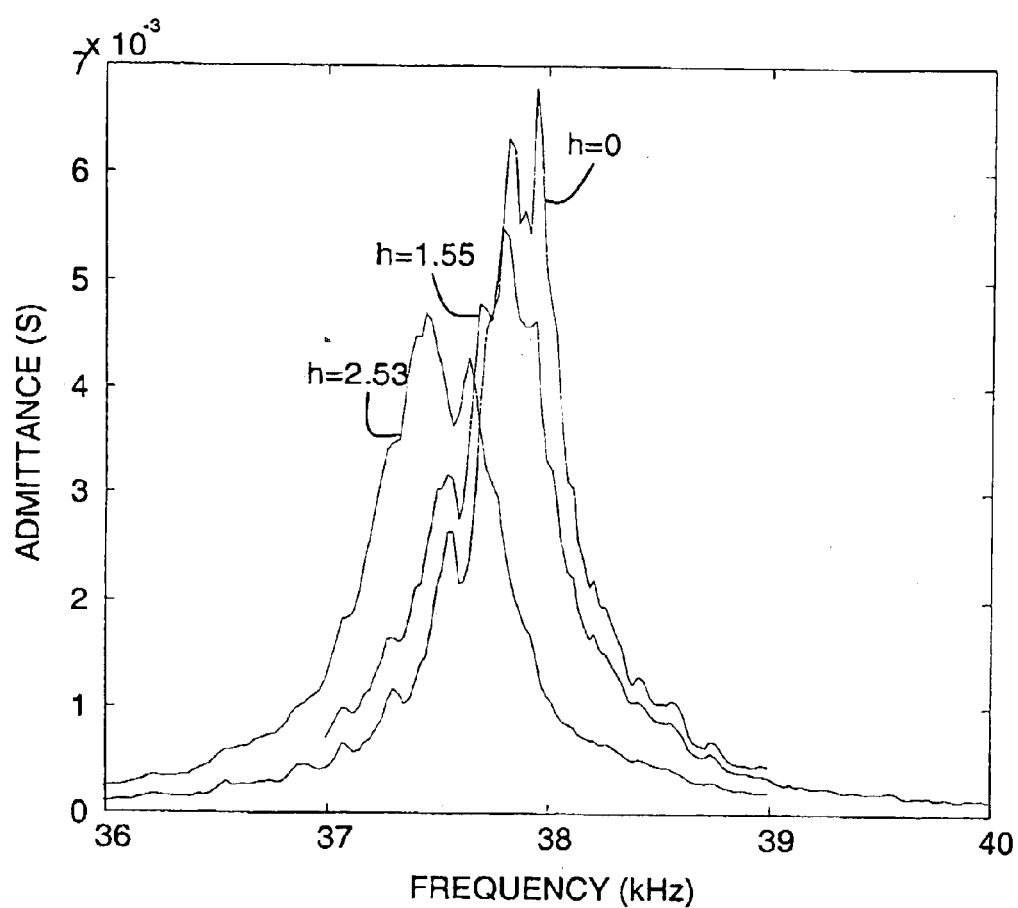
FIG. 4 illustrates the shift of the resonant frequency with increasing wax deposition at ambient pressure.

The resonant frequency of an ultrasonic transducer and horn also decreases when organic deposits, such as wax, form on the tip of the horn. FIG. 4 shows the admittance spectra of a 40 kHz ultrasonic transducer and metal horn immersed in water at ambient pressure with wax of various thicknesses attached to the tip of the horn. The resonant frequency of the transducer decreases by 180 Hz per millimeter of wax of density 0.79 g/cm³ when the horn is immersed in water at ambient pressure.

(II) Acoustic Scale/Deposits Cleaning

The inorganic and organic deposits that accumulate on the tip of the horn can be removed by applying a high alternating voltage to the transducer. The strain produced in the transducer and the attached horn breaks the bond between the horn tip and the deposit and the tip is cleaned. The acoustic deposits sensor can therefore be self-cleaning. The acoustic scale/deposits sensor is also able to clean scale from the surfaces of other components, which are either in close proximity to the tip of the horn or incorporated into it.

The scale was deposited on the tip of a metal horn connected to a 20 kHz ultrasonic transducer. The horn and transducer were housed in the cap of a cell that can be pressurised to 340 bar (5000 psi). The area of the horn tip is 2.87 cm², the average scale thickness is 1.47 mm and the scale density is 4.50 g/cm³. A high voltage was applied to the transducer and the horn was sonicated in a pressure cell at a hydrostatic pressure of 136 bar (2000 psi). All of the inorganic scale was removed from the tip of the horn.

Figure 5:
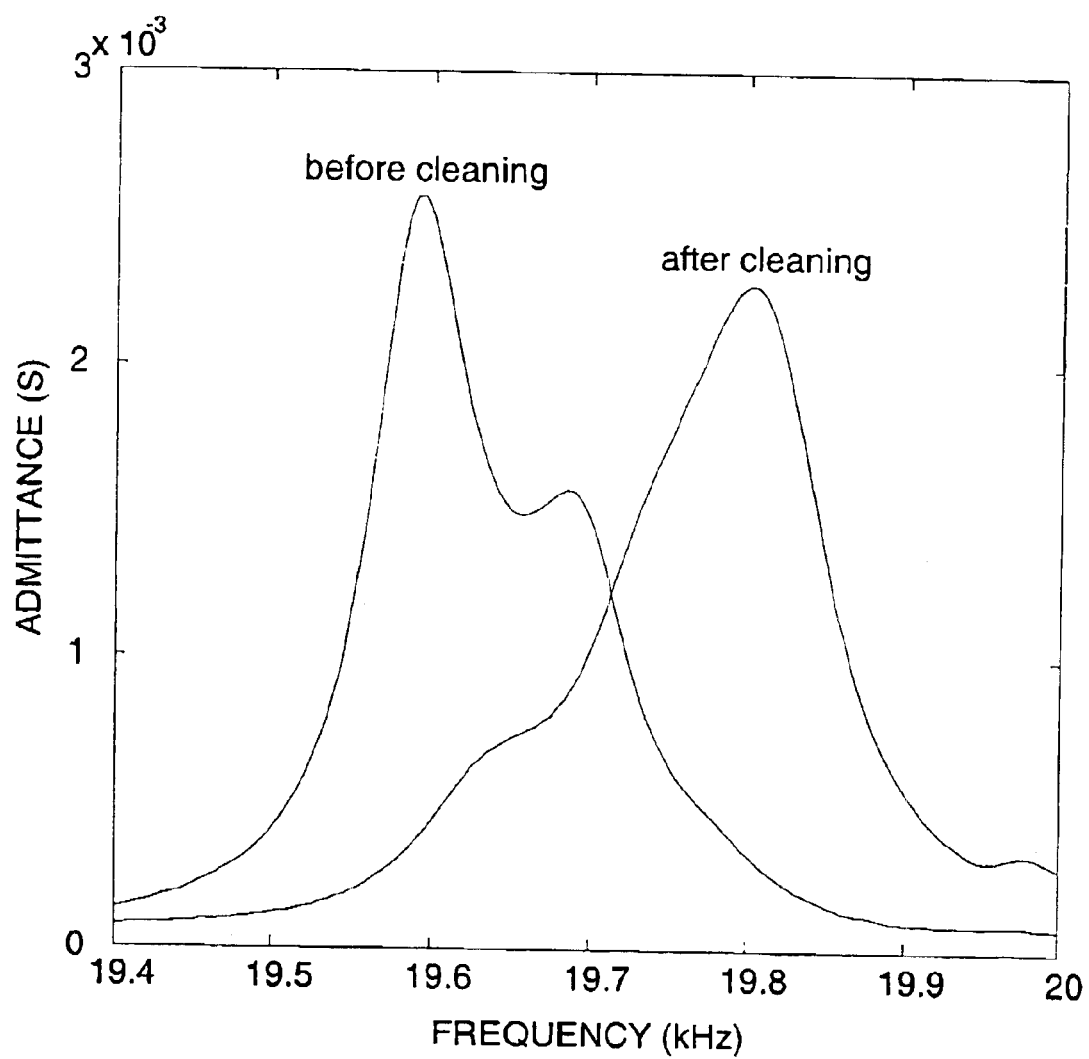
FIG. 5 illustrates the shift of the resonant frequency after cleaning the tip of a sensor.

FIG. 5 compares the admittance spectra of the acoustic transducer and metal horn before and after acoustic cleaning at 136 bar (2000 psi). The resonant frequency of the ultrasonic transducer and metal horn changed by 210 Hz after sonication.

Figure 6:
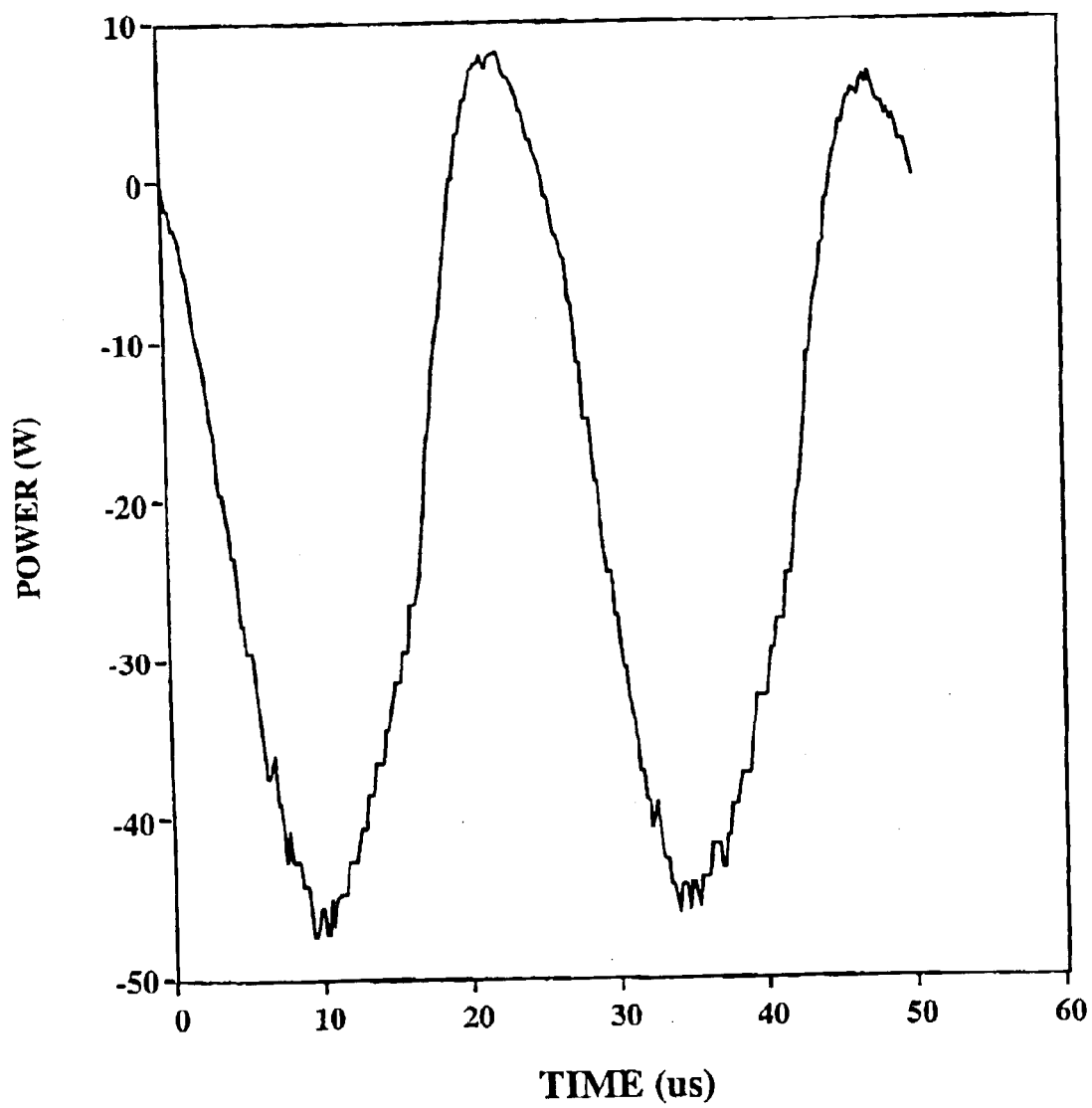
FIG. 6 illustrates the power supply used to remove deposits from a surface exposed to wellbore fluids.

The electrical power that is required by the transducer to remove the scale from the tip of the horn can be determined from the input voltage and current. The frequency of the input voltage and current is 19.84 kHz, which compares to a value of 19.81 kHz obtained from the admittance spectrum of the cleaned horn. The scale, which consisted of a deposit with a density of 4.50 g/cm³ and a thickness of 1.47 mm, was removed from the metal horn at a hydrostatic pressure of 136 bar (2000 psi). FIG. 6 shows the input power waveform supplied to the transducer during the cleaning of the scale. The modulus of the time-averaged input electrical power of the waveform shown in FIG. 6 is 20.4 W.

(III) Some Applications of an Acoustic Deposits Sensor and Cleaner

According to the invention a permanent scale/deposits monitor is provided. Ultrasonic transducers, of the type described above, operating over a range of frequencies, typically 10–150 kHz, can be permanently installed in a producing hydrocarbon well to determine the rate of accumulation of scale and other deposits (wax, asphaltene, etc.). The transducers can be deployed at various locations in the well, including surface production facilities such as subsea valves, risers, separators and any associated pipes and conduits, in order to determine the location of scale formation. The transducers can be used to determine the rate of accumulation of scale and other deposits and these measurements can be used to select the appropriate treatment to maintain the productivity of the well, such as the deployment of scale inhibitors or scale dissolvers. The deposits accumulated on the horn attached to the transducer can be cleaned periodically to maintain its sensitivity.

According to the invention the apparatus can be used in the maintenance of intelligent completions. More specifically, the ultrasonic sensor can be used to determine the accumulation of scale, wax or asphaltene on critical downhole equipment, such as chokes, valves and the sliding sleeves on intelligent completion systems. The measurements can be used to select an appropriate treatment to maintain the integrity and operation of the equipment, e.g., deployment of a scale dissolver to remove scale from critical components.

Figure 7:
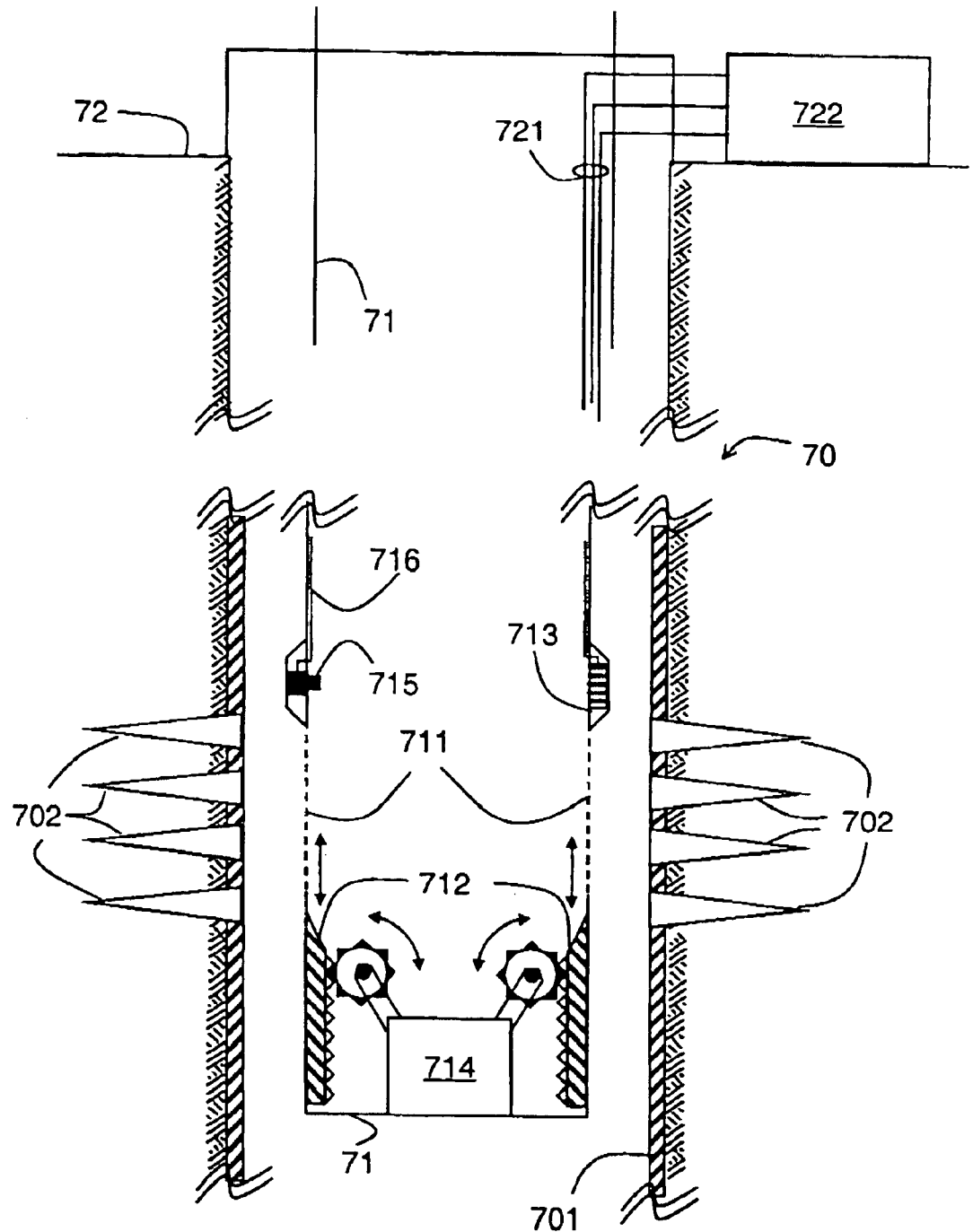
FIG. 7 illustrates a downhole installation in accordance with the invention.

In FIG. 7 reference is made to an "intelligent" completion system deployed to control the flow of wellbore fluid into a production pipe.

FIG. 7 shows a schematic of part of an intelligent completion system. An intelligent completion allows active control of downhole processes such as flow rate measurements and control. A wellbore 70 is shown with a casing 701 installed. At certain locations the casing 701 is perforated by holes 702 to allow wellbore fluid to enter the wellbore. Installed within the wellbore is a production pipe 71 with a slotted section 711. Wellbore fluid enters the production pipe via the slotted section 711. Mounted within the production pipe is a sliding sleeve 712. The sliding sleeve 712 controls the flow of reservoir fluids into the production tubing from a particular section of the well. The flow rate, pressure and temperature of the production fluids are measured by a sensor sub 713 near the slotted section 711 into the tubing. The sliding sleeve 712 is operated by a downhole electrical motor 714 that is powered by means of an electrical cable 721 from the surface 72.

One problem associated with the use of a sliding sleeve is the formation of wellbore deposits, such as inorganic scale or wax, on the sleeve or its track. It is common practice to design the completion hardware such that the electric motor 714 is sufficiently powerful to remove small amounts of scale when the sleeve is moved. However, attempting to remove scale or other deposits by scraping with the sleeve 712 may result in damage to the track and possible jamming. The location of an acoustic scale sensor 715 close to the sliding sleeve 712 will enable the accumulation of deposits on completion hardware to be assessed quantitatively through control equipment 722 located at the surface. Transfer of energy and data signal between control equipment 722 and the sensor 715 is done via wiring 716 run with the production tubing. If scale accumulation on the sleeve is considered to be above a level at which it can be safely operated, then an external scale removal process may be required (e.g., application of a scale dissolver solution).

Alternatively, the control equipment 722 could be used to activate the sleeve periodically or responsive to a threshold amount of deposit as measured by the scale sensor 715. In yet another alternative the control equipment 722 could at least partly be incorporated into the downhole installation. By thus providing a direct feedback control between sleeve and deposit monitor 715, the amount of intervention from the surface can be reduced.

According to the invention, acoustic cleaning of scale and other deposits is provided. The ultrasonic transducer and associated horn can be used to remove scale and other deposits (wax, asphaltene, etc.) from critical components that are used in measurement devices exposed to wellbore/production fluids in the wellbore or on the surface. The components can be part of measurement systems that are either permanently installed in producing hydrocarbon wells or surface facilities or temporarily exposed to the fluids produced by the hydrocarbon well, e.g., on a wireline-deployable tool. Critical components exposed to wellbore fluids that may require cleaning include separation membranes, optical windows and electrical contacts such as electrodes.

Figure 8:
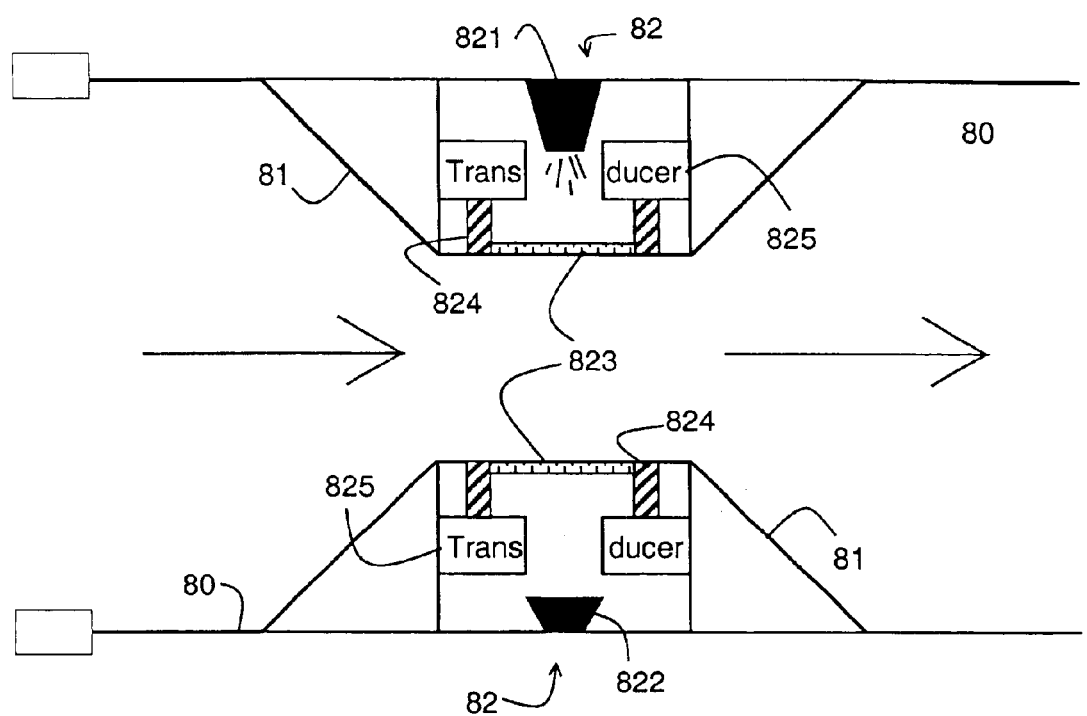
FIG. 8 illustrates a sensor installation with self-cleaning equipment in accordance with the invention.

FIG. 8 refers to a venturi-type flowmeter having a gamma-ray sensor in its constriction section.

It shows a schematic of a gradio-venturi tube 81 located in the tubing 80 of a producing hydrocarbon well. The section of tubing 80 can be located either in a well or on surface facilities. Located within the constriction formed by the venturi 81 is a gamma ray sensor 82. Details of those known components of a gradio-venturi can be found for example in U.S. Pat. No. 5,591,922. The gamma ray sensor, which consists of a gamma ray source 821 (frequently a dual energy source) and a gamma ray detector 822, such as a photomultiplier tube. The gamma rays enter and leave the tube by means of nuclear windows 823 made of a material such as boron carbide. Gamma-ray devices as described above are known as such and described for example in the U.K. Patent Application No. 9919271.8.

A significant problem faced by the gamma ray density measurement is the accumulation of inorganic or organic scales on the nuclear windows 823. For example, the accumulation of small amounts of barium sulphate (barite) scale may result in a serious overestimate of the density of the production fluids. Similarly, the accumulation of radioactive scales on the nuclear windows may give rise to erroneous measurements. The accumulation of organic scales, such as asphaltenes that may contain elements with of high atomic number, can also corrupt the density measurement.

One solution to the problem of deposits accumulation on the nuclear windows 823 is to incorporate them into a high power ultrasonic transducer and horn as is the subject of the present invention (see FIG. 1 above). FIG. 8 shows the two windows located in a hollow horn 824 and transducer 825; the windows 823 are cleaned by operating the transducer in its high power mode. The accumulation of deposits on the windows can be measured by a shift in the resonance frequency of the transducer and horn, as described above.

The gradio-venturi tube of the type above can be located either on the surface or downhole, e.g., as part of an intelligent completion system.

FIG. 9 shows further examples of the use of an ultrasonic transducer and horn to clean measurement devices that may be deployed in a producing hydrocarbon well or at surface installation monitoring the flow of hydrocarbon from the well.

FIG. 9A shows a schematic of an optical window 931 located at the tip of a horn 93 attached to an ultrasonic transducer 91. The optical window 931, which can be made of a suitably resistant material such as diamond or sapphire, can be connected to a source and detector using an optical fibre 95 or other optical conduit such as a light pipe. The optical transmission of the window can be maintained by removing deposits of organic and inorganic scales with ultrasonic cleaning. The accumulation of deposits on the optical window can be determined by either the decreased transmissivity of the window or the change in the admittance spectrum of the transducer 91 and horn 93 assembly. The optical windows can be located either in a producing oil well, on a permanent of quasi-permanent basis, or on the surface facilities. The acoustic cleaning of optical windows can also be applied to wireline logging tools, such as the optical windows used in the Optical Fluid Analyser in Schlumberger's Modular Dynamics Formation Tester tool (described in U.S. Pat. No. 4,994,671) or the windows used in the optical probes to monitor multiphase production from hydrocarbon wells, as described in U.S. Pat. No. 5,831,743.

Figure 9B:
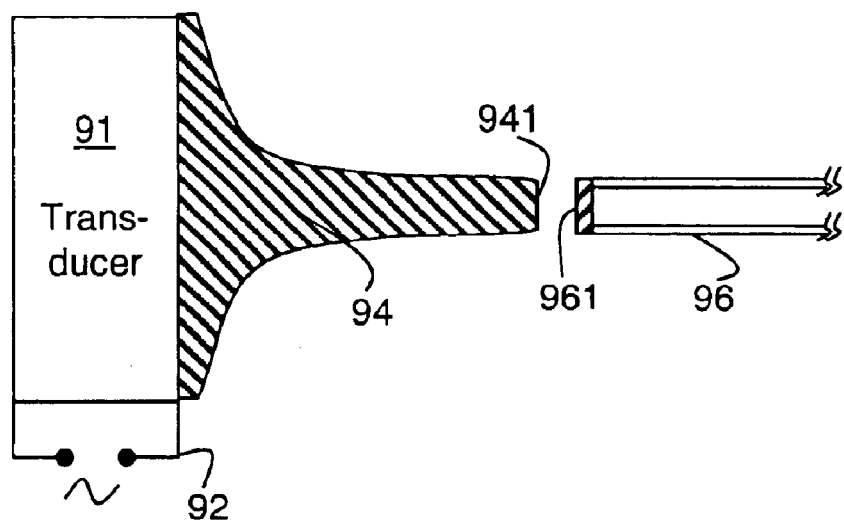

FIG. 9B shows a schematic of an ultrasonic transducer 91 and horn 94 used to clean the membrane 961 of an ion selective electrode 96 that could be used to measure the activity of an ionic species in the water produced from a hydrocarbon well. The performance of the membrane 961 is maintained by the cleaning action of the ultrasonic transducer 91 and horn 94, which are in close proximity to the membrane. The ultrasonic cleaning technique can be used to maintain the permeability of membranes used to separate various components from the fluids produced from hydrocarbon wells, e.g., gas extraction membranes, oil-water separation membranes. Note that a separation membrane and electrode can also be incorporated into the horn coupled to a transducer. The separation membranes can be similarly located in a producing wellbore or in the surface facilities of a producing well.

According to the invention, a method for the identification of scale type is provided. The resonant frequency of the transducer and horn responds to the mass of the attached deposits and it may not be possible to identify the type of scale deposit in the absence of other measurements. One of a variety of measurements could be used to identify the type of scale deposit accumulated on the acoustic horn and thus enable acoustic scale sensor to measure the thickness of the deposit. Two examples are give. Firstly, a spectroscopic measurement could be employed, using an optical widow of the design shown in FIG. 9A. The scale type can identified by a total internal reflection spectroscopic technique, such as infrared spectroscopy, or Raman spectroscopy, which, as reflection and scattering techniques, are insensitive to the thickness of the scale layer. A second possible technique is to use a second acoustic sensor, embedded in the acoustic horn, to measure the acoustic transit time through the scale deposit.

FIG. 10 shows a schematic of the acoustic sensor used to measure the acoustic transit time $\Delta T_t$ through the scale film. This acoustic sensor could be used either downhole or above ground on the surface facilities. Pulsed ultrasound is emitted from an emitting transducer 981 and the reflections are collected by a second receiving transducer 982. The acoustic impedance Z of the scale layer 99 can be estimated by the measured values of the mass W of scale attached to the acoustic horn 97 and $\Delta T_t$. The thickness of scale h attached to the horn is related to W by $$h = \frac{W}{\rho_s A} \quad [1]$$

where $\rho_s$, is the density of the scale and A is the area of the tip of the horn. The thickness h is related to $\Delta T_t$ by $$h = \frac{\Delta T_t V}{2}, \quad [2]$$

where V is the velocity of sound in the scale layer. The combination of eqn. [1] and [2] gives $$Z = \rho_s V = \frac{2W}{\Delta T_t A}. \quad [3]$$

The scale type can be discriminated by the measured value of Z. Table 4 shows the values of the acoustic impedance Z as a function of scale type. When Z is identified the thickness h of the scale deposit can be calculated using eqns. [1] or [2] using the known values of V and $\rho_s$.

TABLE 4

Values of the acoustic impedance Z for various inorganic scales.

| Scale type | Acoustic impedance Z (kg/m$^2$s × 10$^{-6}$) |
|---|---|
| calcite | 17.6 |
| anhydrite | 18.0 |
| celestite | 19.1 |
| barite | 19.9 |

According to the invention monitoring scale/deposits removal techniques are provided. The acoustic scale sensor can be used to evaluate the efficiency of an external scale removal treatment process, such as a scale dissolver solution or a physical scale removal technique. The scale removal treatment can be monitored in real time using the change in the resonant frequency of the transducer and horn. The acoustic scale monitor can therefore be used as part of a scale maintenance service that monitors scale accumulation and evaluates the cleaning/removal process. The maintenance service can be applied to the accumulation of scale both in a producing wellbore or in the surface equipment.

According to the invention, fluid composition and pressure effects can be determined. The resonant frequency of the ultrasonic transducer and horn with no deposits attached depends on the composition of the fluid with which it is in contact and its hydrostatic pressure. A change in the composition of the produced fluid or its hydrostatic pressure may therefore obscure the change in resonant frequency due to the accumulation of inorganic or organic deposits. A change in resonant frequency due to a change in fluid properties can be measured using a second matched transducer and horn, which is in close proximity to the scale detector. The second transducer is cleaned frequently to ensure that the horn is always free from inorganic and organic scales and that the changes in its resonant frequency are solely caused by changes in fluid composition and pressure.

Surface Modification of Acoustic Horn. An important aspect of a scale/deposits sensor permanently installed in a producing hydrocarbon well or in the surface facilities is that the rate of accumulation of deposits must be the same as that of the region of the wellbore it is monitoring. The composition and morphology of the surface of the tip of the horn should be such as to give the same rate of scale accumulation as the solid surfaces in the close environs of the sensor. The surface of the horn tip should be suitably controlled by the choice of material and/or coating. Th material and coating used to fabricate the horn should be able to withstand repeated sonication.

Size of Transducer and Horn. The size of an ultrasonic transducer and horn may be a critical issue for the permanent placement of such a device for scale/deposits monitoring. The size of the transducer and horn are largely determined by the desired frequency of operation and the materials use to them. High power ultrasonic transducers and horns in the size range 5–6 cm, which operate in the frequency range 89–113 kHz, have been reported by Lal and White. See, Lal, A. and White, R. M., "Silicon microfabricated horns for power ultrasonics", *Sensors and Actuators*, A54, 542–546 (1996). The acoustic horns were microfabricated from silicon wafers.

While preferred embodiments of the invention have been described, the descriptions and examples are merely illustrative and are not intended to limit the present invention.

What is claimed is:

1. A deposit monitoring apparatus located in a hydrocarbon wellbore comprising:
   an acoustic device for operating in a resonance mode which is longitudinal including a monitoring surface directly exposed to fluids in a hydrocarbon wellbore, wherein the deposition of material on the monitoring surface is monitored by measuring a change in resonance frequency of the acoustic device; and
   a power supply for supplying said acoustic device with electrical energy.

2. The apparatus of claim 1, wherein the acoustic device is mounted either permanently or quasi-permanently in the wellbore.

3. The apparatus of claim 1, wherein the acoustic device further comprises a transducer, and a focussing element coupled to the transducer.

4. The apparatus of claim 3, wherein the focussing element is an acoustic horn.

5. The apparatus of claim 1, wherein the resonance frequency of the acoustic device is in the range of 10 kHz to 150 kHz.

6. The apparatus of claim 5 wherein the resonance frequency of the acoustic device is in the range of 50 kHz to 100 kHz.

7. The apparatus of claim 1, wherein the monitoring surface is located on or near one of the following devices switches, valves, sleeves, mandrels, downhole separators and sensors located in the wellbore.

8. The apparatus of claim 1 further comprising a deposit removal system for at least partially removing the deposition from the monitoring surface, the deposit removal system being in a control loop with said deposit monitor.

9. The apparatus of claim 8, wherein the deposit removal system includes a deposition inhibiting or removing chemical agent.

10. The apparatus of claim 8, wherein the deposit removal system uses the acoustic device to exert a physical force onto the deposited material.

11. The apparatus of claim 8, wherein the deposition removal system is near a sensor having a surface exposed to the fluids and the deposition removal system is for removing deposits from said exposed surface.

12. The apparatus of claim 11, wherein the sensor is selected from a group comprising optical sensors, electro-chemical sensors, or acoustic sensors.

13. The apparatus of claim 11, wherein the exposed sensor surface is selected from a group comprising optical windows, membranes, or sensitive areas of acoustic sensors.

14. The apparatus of claim 1, comprising an additional sensing system to analyze material deposited on the monitoring surface.

15. A monitoring apparatus located in a hydrocarbon wellbore comprising:
   a monitor for measuring characteristics of fluids in the hydrocarbon wellbore, the monitor having a monitoring surface that is directly exposed to fluids in the hydrocarbon wellbore;
   a deposit removal system including an acoustic device for exerting a physical force on the monitoring surface to at least partially remove a deposition of material from the monitoring surface; and
   a power supply for supplying said acoustic device with electrical energy, wherein the monitor further uses the acoustic device, said acoustic device to be operated in a resonance mode, wherein the monitor measures deposition of the material on the monitoring surface by measuring a change in resonance frequency of the acoustic device and wherein the acoustic device operates in a longitudinal mode.

16. The apparatus of claim 15, wherein the acoustic device further comprises a transducer, and a focussing element coupled to the transducer.

17. The apparatus of claim 15, wherein the resonance frequency of the acoustic device is in the range of 10 kHz to 150 kHz.

18. The apparatus of claim 15, wherein the deposit removal system includes a deposition inhibiting or removing chemical agent.

19. A monitoring apparatus located in a hydrocarbon wellbore comprising:
   a monitor for measuring characteristics of fluids in the hydrocarbon wellbore, the monitor having a monitoring surface that is directly exposed to fluids in the hydrocarbon wellbore;
   a deposit removal system including an acoustic device for exerting a physical force on the monitoring surface to at least partially remove a deposition of material from the monitoring surface; and
   a power supply for supplying said acoustic device with electrical energy, wherein the monitor is selected from a group comprising optical sensors, electro-chemical sensors, nuclear sensors, separation membranes, or acoustic sensors separate from the force exerting acoustic device.

20. The apparatus of claim 19, wherein the monitor is a gamma ray density measurement system.

21. The apparatus of claim 20 wherein the monitoring surface is a nuclear window.

22. The apparatus of claim 19, wherein the monitor is an optical fluid analyzer.

23. The apparatus of claim 22 wherein the monitoring surface includes an optical window.

24. The apparatus of claim 19, wherein the monitor is used to measure activity of an ionic species contained in the wellbore fluid.

25. The apparatus of claim 24 wherein the monitoring surface is a membrane of an ion selective electrode.

26. The apparatus of claim 19, wherein the monitoring surface is a separation membrane.

27. A deposit monitoring apparatus located in a hydrocarbon wellbore comprising:
   an acoustic device for operating in a resonance mode including a monitoring surface directly exposed to fluids in a hydrocarbon wellbore, wherein the deposition of material on the monitoring surface is monitored by measuring a change in resonance frequency of the acoustic device, and wherein by measuring said change in resonance frequency of the acoustic device a thickness of deposited material of 600 microns can be distinguished from a thickness of deposited material of 1050 microns; and
   a power supply for supplying said acoustic device with electrical energy, wherein the acoustic device operates in a longitudinal mode.

28. The apparatus of claim 27, wherein the acoustic device further comprises a transducer, and an acoustic horn coupled to the transducer.

29. The apparatus of claim 27, wherein the resonance frequency of the acoustic device is in the range of 10 kHz to 150 kHz.

* * * * *